United States Patent [19]

Backman

[11] Patent Number: 4,673,640
[45] Date of Patent: Jun. 16, 1987

[54] REGULATED PROTEIN PRODUCTION USING SITE-SPECIFIC RECOMBINATION

[75] Inventor: Keith C. Backman, Bedford, Mass.

[73] Assignee: Biotechnica International, Inc., Cambridge, Mass.

[21] Appl. No.: 605,488

[22] Filed: Apr. 30, 1984

[51] Int. Cl.[4] .................. C12P 21/00; C12N 15/00; C12N 1/20; C12N 1/00; C07H 15/12
[52] U.S. Cl. ........................................ 435/68; 435/70; 435/172.3; 435/253; 435/317; 536/27; 935/42; 935/43; 935/73
[58] Field of Search ............... 435/317, 68, 70, 253, 435/72.3; 935/73, 42, 43; 536/27

[56] References Cited

PUBLICATIONS

Murray, In *Lambda II*. R. Hendrix et al., eds. Cold Spring Harbor Laboratory, 1983, pp. 395–432.
Podhajska, *Gene* 40: 163–168 (1985).
Proceedings of the XV International Congress of Genetics (1983) New Delhi, India—Table of Contents and Author Index.
*Cell*, "Structural Features of Site-Specific Recombination at a Secondary att Site in galT" Bidwell et al. Bo. 16, (1979).
*Cell*, "A Secondary Attachment Site for Bacteriophage in trpC of *E. coli*" Christie et al., vol. 16, (1979).
Campbell et al., "Evolution of Lambdoid Phages" in *Lambda II* (Hendrix, Ed) Cold Spring Harbor 1983.
Silverman et al., (1981) *Virology* vol. 127:17–26.
Iino et al., "Trans-acting Genes of Bacteriophages of P1 and Mu Mediate Inversion of a Specific DNA Segment Involved in Flagellar Phase Variation of Salmonella", Cold Spring Harbor Symposium on Quantative Biology, 45:11–16, (Cold Spring Lab. N.Y., 1981).
Plasterk (1983) *Virology* 127:24–36.
Echols et al., "Control of Integration and Excision" *Lambda II* (Hendrix et al., Ed.) Cold Spring Harbor Laboratory, 1983, pp. 75–92.

Primary Examiner—Thomas S. Wiseman
Assistant Examiner—Thomas D. Mays

[57] ABSTRACT

In vivo regulation of protein production is achieved by rearranging DNA segments comprising a protein-producing gene (i.e., protein-encoding DNA as well as regulatory DNA to effect the expression of the protein-encoding DNA in the host), in response to a change in an environmental condition such as temperature. The rearrangement is synchronized and directional (irreversible) in members of the cell population, because it is catalyzed by a lambda phage site-specific recombination enzyme system that operates on a pair of lambda phage attachment sites to rapidly drive the rearrangement and to avoid the reverse reaction. The cells include means to produce the lambda enzyme system in response to the change in environmental condition. By engineering one of the attachment sites within the gene that produces the protein whose production is to be regulated (yielding two gene segments), the synchronized rearrangement operates to change the gene from one configuration to another. In only one of these configurations are the gene segments positioned and oriented for protein production. Specifically, the protein-producing configuration is: gene segment one-attachment site-gene segment two. The attachment site is exogenous to the gene, i.e, it does not occur in that location naturally and is positioned there by engineering techniques. The regulated protein production is useful, e.g., in fermenting the desired product, by allowing cell growth to proceed in the absence of product formation. When the desired cell mass is achieved, product production is enabled by the rearrangement.

27 Claims, 6 Drawing Figures

REGULATED PROTEIN PRODUCTION USING SITE-SPECIFIC RECOMBINATION

BACKGROUND OF THE INVENTION

This invention relates to DNA for transforming cells to enable regulated in vivo protein formation, to the cells that are used in the transformation, to precursors for making such transforming DNA, and to methods of using the DNA.

It is often useful to engineer an organism with genetic information whose expression is subject to in vivo control. For example, when using engineered organisms to produce a desired compound, it is desirable to control expression of relevant genes (genes coding for the compound itself, for a compound precursor, or for enzymes in the compound's synthetic pathway) so that compound production is reduced or prevented during the organism's exponential growth phase, because compound production may be deleterious to the organism or may slow its growth due to energy demands. By controlling compound production in the growth phase, the engineered organism may grow more rapidly and may not be at a competitive disadvantage with respect to nonproducing organisms (e.g. mutants). Once a satisfactory population of engineered organisms is obtained, they must be made capable of product manufacture. Preferably, such regulatory control is strong; that is, compound production should be dramatically reduced or eliminated when desired, and compound production should be as copious as possible when desired. Apart from compound biosynthesis it may be desirable to control genetic expression to control other traits of engineered organisms.

Some gene promoters are influenced by regulatory effector molecules which interact with sites at or near the promoter to enable or prevent expression of structural genes under the promoter's control. Thus, expression of a structural gene that has been introduced to an organism may be influenced by engineering the gene to be controlled by such a regulated promoter and then using the regulatory effector molecule to control the gene's expression [Backman et al. (1976) Proc. Nat'l Acad. Sci. USA 71: 4174.].

Other gene promoters are essentially unregulated. These promoters tend to be much stronger (i.e., they induce greater expression of structural genes under their control) than regulated promoters. Until now, however, very strong unregulated promoters have been difficult to use because they cannot be cloned unless followed by an effective signal for termination of transcription and because regulation may be desirable for the reasons discussed above.

Finally, it is known that in certain systems, a DNA segment reversibly inverts, creating a population of organisms that is heterogenous in that in some organisms the DNA segment is in one orientation and in others it is in the opposite orientation. For example, Silverman et al. report an analysis of the genes involved in the DNA inversion responsible for oscillation of flagellar phenotypes of Salmonella, ["Analysis of the Functional Components of the Phase Variation System", Cold Spring Harbor Symposium on Quantitative Biology, 45: 17-26, (Cold Spring Harbor Laboratory, New York, (1981)]. Silverman et al. disclose that the Salmonella DNA inversion is a site-specific recombination event involving 14 bp inverted repeat sequences.

Iino et al. disclose that certain bacteriophage (Pl and Mu) express a DNA inversion factor which is effective to increase the frequency of flagellar phase variation in Salmonella by increasing reversible DNA inversion in that organism, "Trans-acting Genes of Bacteriophages of Pl and Mu Mediate Inversion of a Specific DNA Segment Involved in Flagellar Phase Variation of Salmonella", Cold Spring Harbor Symposium on Quantitative Biology, 45:11-16, (Cold Spring Laboratory New York, 1981)].

Struhl (1981) J. Mol. Biol. 152:517-533 disclose that the bacteriophage lambda int gene mediates many events including deletion events which randomly generate new gene sequences some small fraction of which may have genetic activity.

SUMMARY OF THE INVENTION

In one aspect, the invention features, generally, DNA capable of transforming a cell to allow regulated in vivo formation of a protein-producing DNA segment made up of at least two subsegments which are positioned so that a specified end of one subsegment is adjacent a specified end of the other subsegment. In the transforming DNA, the specified end of one subsegment is placed adjacent a first DNA site for enzymatic site-specific recombination, and the specified end of the other subsegment is placed adjacent a second DNA site for enzymatic site-specific recombination, remote from the first enzyme-specific site. At least one subsegment is "exogenous" to (i.e., it does not naturally occur adjacent) its enzyme-specific site. In vivo exposure of a transformed population to a selected enzyme system causes synchronized DNA rearrangement, forming the protein-producing DNA segment and favoring such formation over enzymatic reversal of the DNA rearrangement which would re-form the subsegments. As used herein, enzymatic site-specific recombination means recombination between DNA sequences at specific DNA sites, which is catalyzed by an enzyme specific for those recombination sites. "Synchronized" rearrangement means rapid rearrangement in a substantial (at least 65%) percentage of the transformed organism population to the desired protein-producing DNA segment, without significant reversal of the rearrangement, that is, re-formation of the subsegments from the desired segment.

In preferred embodiments, the enzyme system is a phage enzyme system for site-specific recombination and the enzyme-specific sites are phage attachment sites. The transforming DNA may be a continuous strand, in which case excission of the DNA between the attachment sites is achieved by using sites having the same absolute orientation; alternatively, inversion of the DNA between the sites is achieved by using sites having opposite absolute orientations. If the transforming DNA is made of two separate strands, then the rearrangement involves integration of the two strands. The complementary enzyme-specific site pair may be attP and attB sites, in which case the enzyme system comprises a phage integration (Int) enzyme; alternatively, the site pair may be attL and attR sites, in which case the enzyme system comprises phage integration (Int) and excission (Xis) enzymes. The two DNA subsegments may be, respectively, a structural gene (including a correctly framed translation initation sequence) and a promoter for that structural gene in which case, the rearranged protein-producing DNA comprises, in sequence: the promoter, the translation start signal and the structural gene; these may be extraneous DNA between the promoter and translation start site, for example a recombination site. Specifically, an unregulated promoter may be used, in which case the transforming DNA may of necessity include a transcription stop site on the side of the enzyme-specific site opposite from the promoter associated therewith. Alternatively, the DNA subsegments may be portions of the structural gene coding for a biologically active protein, which portions themselves code for biologically inactive protein segments. Expression of the enzyme system is subject to regulatory control such as the temperature sensitive repressor control of the lambda phage enzyme system.

In another aspect, the invention features a method of regulated protein biosynthesis comprising transforming a cell with the above-described transforming DNA, culturing the transformed cell to a desired population of cells which do not produce the protein, exposing the transforming DNA within the cell population to the enzyme system causing synchronized DNA rearrangement to form the protein-producing DNA segment, and then allowing the cells to synthesize the protein.

In a third aspect the invention features a precursor to the above-described transforming DNA comprising the two sites for enzymatic site-specific recombination, a restriction endonuclease cleavage site which is unique to the DNA precursor positioned adjacent one of the enzyme-specific sites, and a promoter sequence positioned adjacent the other enzyme-specific site so that its promoting function is directed toward that site.

The invention enables effective regulation of protein production. One enzyme molecule can rearrange a large number of DNA molecules, so that control exerted over the enzyme is amplified. Moreover, the invention enables use of promoters which are stronger than those regulated by regulatory effector compounds because the strong promoter can be controlled by a transcription stop sequence until gene expression is desired. The invention improves the efficiency of cell growth and culturing steps because during cell growth and culturing, the genetic information necessary for the production of the protein is simply not present in a functional form in the cell and therefore cannot be expressed to hinder cell growth. Once protein production is desired, however, the necessary genetic material is efficiently created. Other features and advantages of the invention will be apparent from the following description of the preferred embodiments and from the claims.

DESCRIPTION OF THE PREFERRED EMBODIMENT

STRUCTURE

The two sites shown in the DNA diagrams in FIGS. 1-4 which are specific for enzymatic reciprocal recombination are phage attachment sites, labeled respectively attL and attR; that is, they are sites at which a phage enzyme system catalyzes site-specific recombination. Specifically, the pair of sites shown in the figures is functionally equivalent to BOP' (or attL) and POB' (or attR), where O is a region of homology between the chromosome of a bacterial host and an infecting phage, B and B' are bacterial chromosome regions flanking O, and P and P' are phage DNA regions flanking O. Alternatively, the pair BOB' (or att B) and POP' (or att P) could be used. Functional equivalency means the site is recognized by a site-specific recombination enzyme system.

No matter which pair is used, it should be matched to the enzyme system that is to be used to effect the desired rearrangement, so that the system will be driven substantially to complete the rearrangement and to avoid the opposing reverse reaction which forms the DNA fragments from the desired protein-producing DNA sequence. The attL/attR pair is matched to the enzyme system for excision which, in the phage lambda system, comprises both the Int and Xis proteins. The attB/attP pair is matched to the enzyme for integration which, in the phage lambda system, is the Int protein without the Xis protein. Finally, functioning of both the Int and the Int/Xis enzyme systems requires an integration host factor (IHF), a protein produced by the host bacterium.

Figure 5:
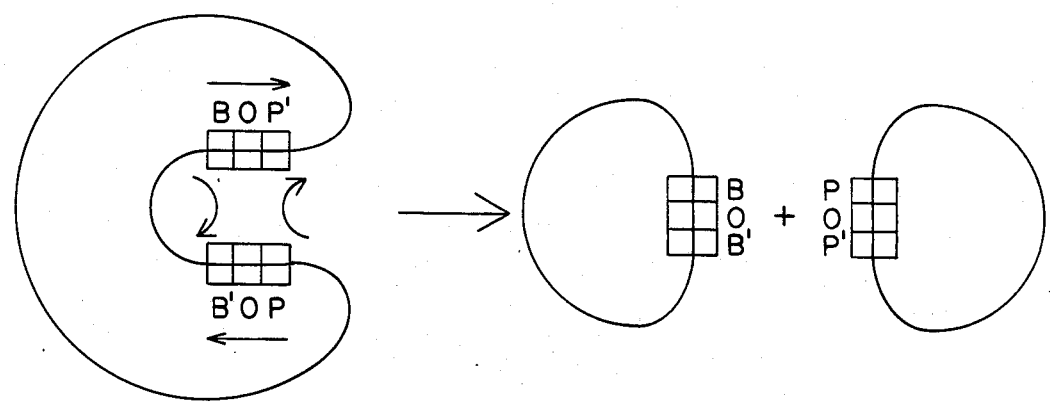
FIG. 5 is a DNA diagram depicting an excision event.
Figure 6:
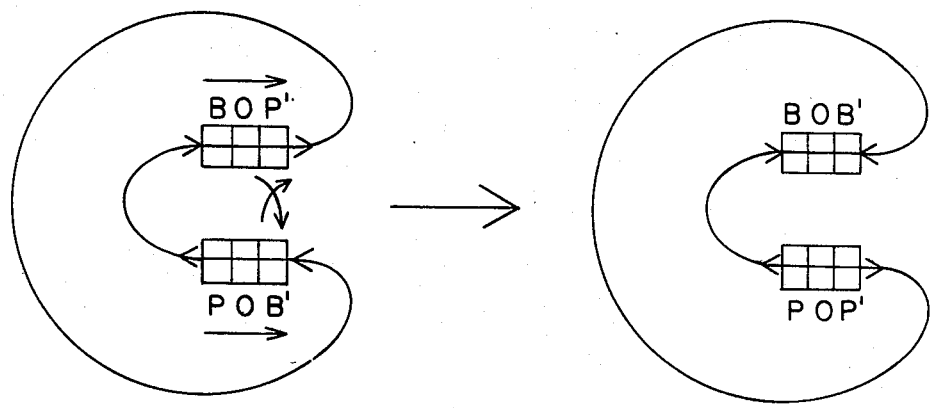
FIG. 6 is a DNA diagram depicting an inversion event.

The desired rearrangement may be excission, integration, or inversion, depending upon the form of the transforming DNA and the relative orientation of the enzyme specific sites. As shown in FIGS. 5 and 6 excission will be strongly favored if the sites are oriented in the same absolute direction and inversion will be strongly favored if the sites are oriented in the opposite absolute orientation. For example BOP' has the same absolute orientation as POB' (FIG. 5), and BOP' has the opposite orientation as B'OP (FIG. 6).

Integration is the reverse of the process depicted in FIG. 5.

Figure 4:
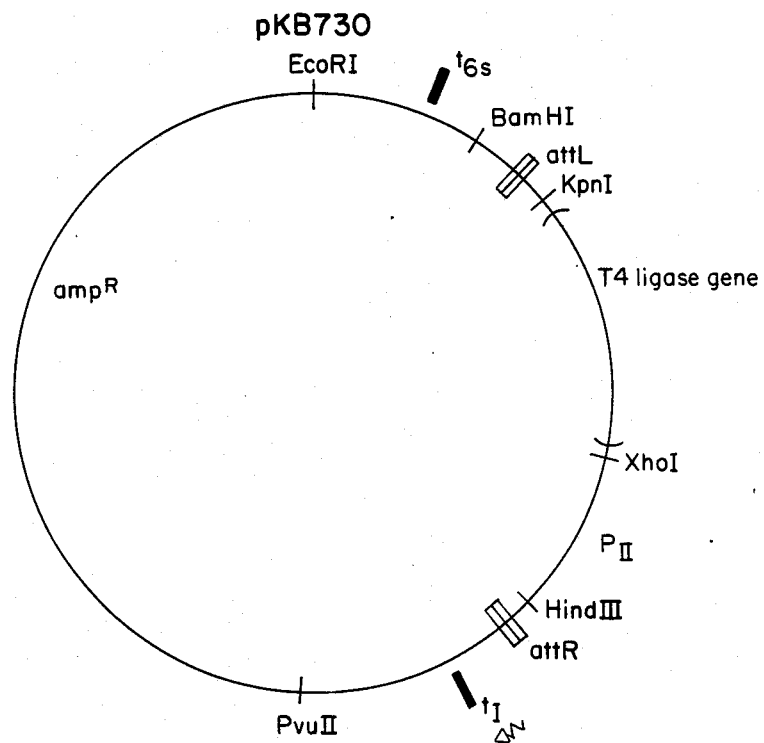
FIG. 4 is a diagram of the DNA of plasmid pKB730 showing certain sites thereon.

In addition to the enzyme specific sites described above, the transforming DNA includes two DNA subsegments which are to be brought into juxtaposition by the DNA rearrangement. FIG. 4 shows a strong, unregulated constitutive promoter segment as one of the subsegments and a structural gene sequence as the other subsegment. Adjacent the structural gene segment is a translation initiation site, positioned in reading frame with, and on the same side of the recombination site as, the structural gene, so that after rearrangement, the rearrangement site which separates the promoter from the structural gene is not translated into an extraneous amino acid sequence. Thus, after rearrangement, the two subsegments do not necessarily abut one another. In FIG. 4, the promoter is labeled PII to designate the gene II promoter from phage m13. The structural gene in the transforming DNA codes for T4 DNA ligase from phage T4.

The PII promoter is oriented to promote transcription toward the adjacent attR site, and the T4 ligase gene is oriented so the end to be transcribed first is adjacent the attL site. Those ends must be juxtaposed to produce an effective T4 ligase-producing gene. $T_I$ is a transcription termination site adjacent the attR site on the side of it opposite to the PII promoter. $T_I$ serves to stop transcription from the unregulated PII promoter, thus preventing wasted cell energy in unproductive transcription before DNA rearrangement is triggered. Transcription starting at PII and terminating at $t_I$ is indicated by a wavy arrow. A second transcription termination site, labeled $t_{6s}$, is positioned near the att L site to prevent transcription into and expression of the structural gene prior to DNA rearrangement.

Plasmid pKB730 also includes a gene for ampicillin resistance ($amp^R$) which is a marker for detecting successfully transformed cells.

CONSTRUCTION

Figure 1:
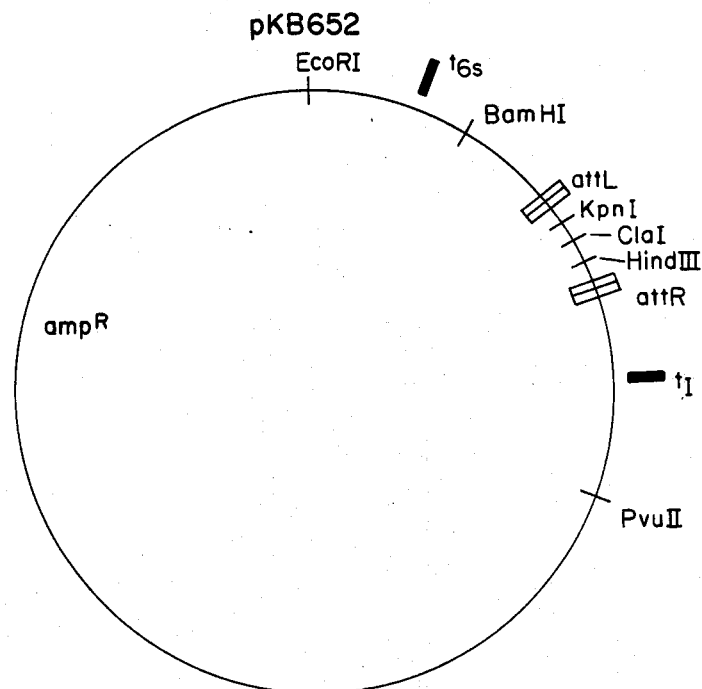
FIG. 1 is a diagram of the DNA of plasmid pKB652 showing certain sites thereon.
Figure 2:
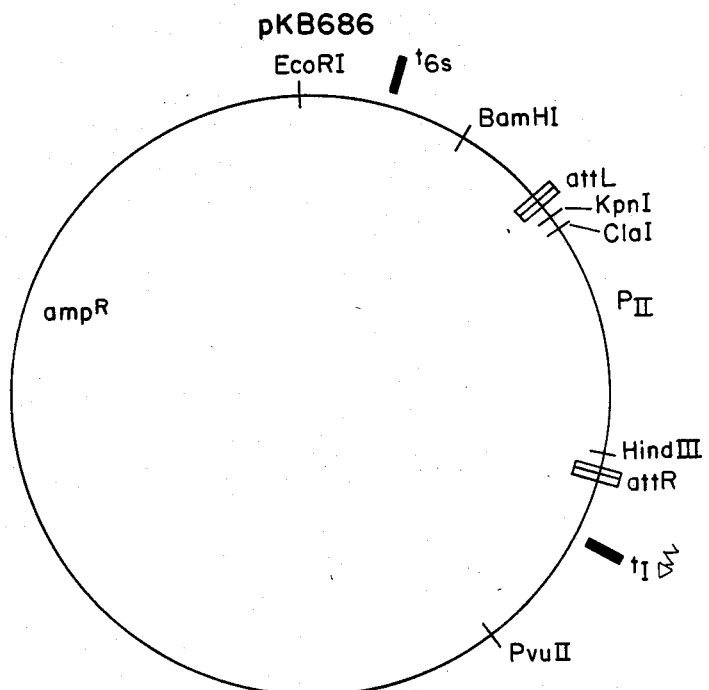
FIG. 2 is a diagram of the DNA of plasmid pKB686 showing certain sites thereon.
Figure 3:
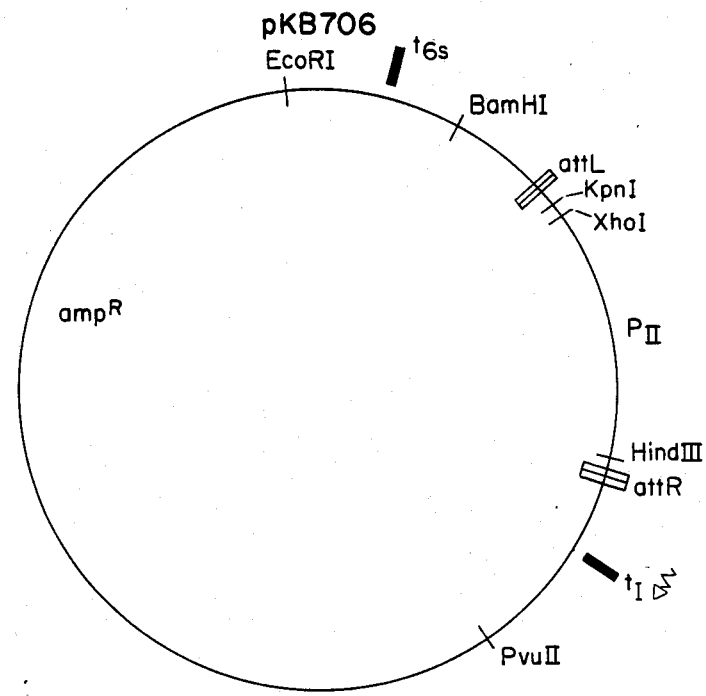
FIG. 3 is a diagram of the DNA of plasmid pKB706 showing certain sites thereon.

The construction of plasmid pKB730 is depicted in FIGS. 1–3. Unless specifically indicated otherwise, recombinant DNA techniques suitable for the steps described are found in Maniatis et al, *Molecular Cloning*, (Cold Spring Harbor Laboratory 1982).

A specific rearrangement vector is constructed to have the following properties: multiple unique cloning sites are bracketed by functional equivalents of lambda attL and attR, and this construction is bracketed by transcription terminators to terminate transcription into and out of the region in one orientation. The construction is described as follows.

DNA fragments corresponding to the region of the lambda attachment site (HindIII at position 27479 to BamHI at position 27972) and the region of the 6S transcript (HinIII at position 44141 to EcoRI at position 44972) are separately cloned from bacteriophage lambda DNA [a commercially available phage; the positions referred to herein are those indicated in Sanger et al., (1982) J. Molec. biol. 162:729–773] onto pBR322 [a commercially available plasmid], yielding pKB603 and pKB602 respectively.

The following pieces of DNA can be prepared from pKB602, pKB603, or pBR322, and assembled in a series of steps whose particulars are not of consequence to the functioning of the completed assembly:

1. a piece carrying the 6s transcription terminator $t_{6s}$ extending from a HaeII site within the 6s transcript gene to a Sau3AI site just past the 6s transcription terminator (the HaeII site is converted to an EcoRI site by means of a linker);
2. a piece carrying a functional equivalent of attL extending from a BamHI site to an AluI site immediately adjacent to the core sequence of attP (the AluI site is converted to a KpnI site by means of a linker);
3. a portion of pBR322 comprising the ClaI and HindIII sites (the ClaI site is joined to a KpnI linker in a manner which regenerates the ClaI site);
4. a piece carrying a functional equivalent of attR extending from a DdeI site immediately adjacent to the core of attP to a HindIII site (the HindIII site might be converted to a PvuII site by treatment with nuclease Sl but it is preferable to use PvuII linkers).

The pieces are assembled and cloned in pBR322 between the EcoRI and PvuII sites. The EcoRI site of fragment 1 is joined to the EcoRI site of pBR322; the Sau3AI site of fragment 1 is joined to the BamHI site of fragment 2, regenerating a BamHI site. The KpnI site of fragment 2 is joined to the KpnI site of fragment 3. the HindIII site of fragment 3 is joined to the DdeI site of fragment 4; since both ends are filled-in prior to joining, a Hind III site is recreated. The PvuII site of fragment 4 is joined to the PvuII site of pBR322. The resulting plasmid is pKB652 (FIG. 1).

A strong constitutive promoter is then cloned into the vector pKB652. In outline, the gene II promoter from a derivative of phage m13 is cloned by standard methods on a piece of DNA which extends from a Sau96I site to an NdeI site. The nucleotide sequence of m13 is published by Van Wezenbeck et al. (1980) Gene 11:129–148. The Sau96I end is converted to a ClaI site, and the NdeI end is converted to a HindIII site by use of linkers in a series of steps, and the resulting promoter-containing piece of DNA is cloned between the ClaI and HindIII sites of pKB652, yielding pKB686 (FIG. 2). Alternatively, a variant of pKB686 is made in which the ClaI site is converted to an XhoI site by means of a linker, yielding pKB706 (FIG. 3). The use of either pKB686 or pKB706 may be preferred depending on circumstances related to the structural gene to be cloned for expression, such as cleavage sites available when cloning the gene.

A piece of DNA carrying the gene for T4 DNA ligase is cloned from phage lambda NM989. [Wilson et al (1979) J. Molec. biol. 132:471–491]. In a series of steps, an AluI site separating the gene from its natural promoter is converted to a KpnI site, and the HindIII site following the gene is converted to an XhoI site. The gene is then cloned into pKB706 between the KpnI and XhoI sites. This yields pKB730 (FIG. 4).

Plasmid pKB686 is deposited with the American Type Culture Collection with accession number ATCC 39671. Plasmid pkB706 is deposited with the American Type Culture Collection with accession number ATCC 39672.

OPERATION

The pKB730 cloning vehicle is used to transform *E. coli* strain KB204, a spontaneous galactose utilizing revertant of derivative of strain M5160][Greer (1975) Virology 132:471–491 (1979)], which contains on its chromosome a defective lambda prophage with a temperature sensitive repressor controlling production of the int and xis genes. Strain KB204 is deposited with the ATCC with ATCC accession number 39670.

The successfully transformed cells are cultured at temperatures too low to inactivate the repressor (e.g. about 30° C). In that state, no rearrangement occurs, and PII-promoted transcription is blocked by termination site $t_f$.

When a desired culture size is achieved, the temperature is increased to inactivate the repressor and thus allow expression of the lambda prophage integration-/excission enzymes Int and Xis.

These enzymes rapidly (well within the cell doubling time) trigger the desired DNA rearrangement, in this case excision to form two DNA molecules from one (see FIG. 5). The enzyme system and the specific sites selected decidedly favor excision and do not allow significant reversal of the rearrangement, because the Int/Xis protein combination favors recombination of the BOP'/POB' pair over recombination of the BOB'-/POP' pair. Therefore, the system favors formation of the desired protein-producing DNA segment which includes the PII promoter adjacent the proper end of the T4 ligase structural gene, and such a structure is formed in at least 65% of the transformed cell population. Where the amount of enzyme system is the limiting factor controlling yield of cells with rearranged DNA, yield may be improved by increasing the copy number or promotor strength for the enzyme-system genes in the transformed cells.

In a lysate from a culture in which rearrangement has been induced, after three hours, a large portion (>10%) of the soluble protein is T4 DNA ligase. Upon purification, a small amount of ligase activity is detected in the uninduced lysate. T4 ligase of about 90% purity is obtained from the induced lysate after a single step elution from a phosphocellulose column.

OTHER EMBODIMENTS

Other embodiments are within the following claims. For example, other site-specific enzyme systems can be used. Other host cells, promoters, and structural genes can be used. Moreover, the subsegments need not be a promoter/structural gene combination but instead can be two segments of a structural gene that codes for a biologically active protein. Neither of the subsegments produces a biologically active protein by itself, but, when combined, the active protein is produced. Thus DNA rearrangement may be used to create the structural gene necessary for activity. The enzyme system can be introduced in other ways, for example by phage-based cloning vehicles.

I claim:

1. A cell population capable of regulated, synchronized, directional DNA rearrangement from a first configuration to a second configuration responsive to a change from a first environmental condition to a second environmental condition, cells in said population comprising:
   (a) DNA encoding a lambda phage site specific recombination enzyme system, said enzyme-encoding DNA comprising int, or a combination of int and xis;
   (b) regulatory DNA positioned to express at least one of said int or xis, said regulatory DNA being effective to cause said expression when said cells are exposed to said second environmental condition and to curtail said expression when said cells are exposed to said first environmental condition;
   (c) a pair of DNA attachment sites of a lambda phage, said sites being capable, in the presence of said enzyme system, of rapidly undergoing site-specific recombination resulting in a change in the DNA from said first configuration to said second configuration, while avoiding the reverse reaction, thus achieving said synchronized directional DNA rearrangement;
   (d) a first segment of a protein-producing gene and a second segment of a protein-producing gene, said segments together comprising protein-encoding DNA and regulatory DNA to express said protein-encoding DNA, said segments being oriented and positioned for protein production only in one of said two configurations, said protein-production configuration being as follows: first segment—attachment site—second segment;
   whereby said environmental change causes a synchronized directional rearrangement of DNA in said cells from said first configuration to said second configuration.

2. The cell population of claim 1 wherein said regulatory DNA comprises a promoter that transcribes through said second gene segment only in said second configuration, whereby said protein is expressed only in said second configuration, and said environmental change results in said protein expression.

3. The cell population of claim 1 wherein said enzyme system consists of the int and the xis gene products of a lambda phage.

4. The cell population of claim 1 wherein said first configuration comprises two DNA molecules, each having one said attachment site, and said rearrangement comprises integration of said two molecules to create a single DNA molecule.

5. The cell population of claim 1 wherein said first configuration comprises a single DNA molecule having said pair of attachment sites spaced apart from each other and having the same absolute orientation, and said rearrangement comprises excision of DNA between said attachment sites to create two DNA molecules, each having one said attachment site.

6. The cell population of claim 1 wherein said first configuration comprises a single DNA molecule having said pair of attachment sites spaced apart from each other and having the opposite absolute orientation, and said rearrangement comprises inversion of DNA between said attachment sites.

7. The cell population of claim 1 wherein said first protein-producing gene subsegment comprises a promoter effective top transcribe said protein-encoding DNA in one said configuration.

8. The cell population of claim 7 wherein said promoter is an unregulated promoter.

9. The cell population of claim 7 wherein said cells comprise a transcription terminator positioned so that, in one said configuration, said promoter transcribes through a said attachment site to said terminator and said second gene segment is not transcribed, and in the other said configuration, said promoter transcribes through a said attachment site and through said second gene segment.

10. The cell population of claim 4 wherein, in said first configuration, each of said two DNA molecules comprises a said gene segment.

11. The cell population of claim 7 wherein, in said first configuration, said two gene segments are positioned between said two attachment sites, and said promoter is oriented to transcribe away from said second gene segment.

12. The cell population of claim 9 wherein said first configuration comprises a single DNA molecule having said pair of attachment sites separated by DNa comprising said two gene segments, said promoter is oriented to transcribe away from said second gene segment, through one of said attachment site to a transcription terminator, and said rearrangement comprises excision of DNA between said attachment sites to create two DNA molecules, one having said promoter positioned to transcribe through one of said attachment site and through said second gene segment, and the other having said transcription terminator.

13. The cell population of claim 1 wherein said pair of DNA attachment sites are attP and attB, and said enyzme system consists of a phage lambda int gene product.

14. The cell population of claim 1 wherein said pair of DNA attachment sites are attL and attR, and said enzyme system consists of a phage lambda int gene product and a phage lambda xis gene product.

15. The cell population of claim 8 wherein said unregulated promoter is the pII promoter comprising a sequence between the Sau 96I site and an NdeI site of phage m13.

16. The cell population of claim 15 wherein attR site comprises a site-specific recombination site between HindIII at position 27479 and DdeI at position 27735 of bacteriophage lambda, and wherein said attL site comprises a site-specific recombination site between AluI at positon 27724 and BAmHI at position 27972 of bacteriophage lambda.

17. The cell population of claim 1 wherein said environmental condition is temperature.

18. The cell population of claim 7 wherein said second protein-producing gene segment comprises a translation initiation signal in frame with DNA encoding said desired protein.

19. The cell population of claim 12 wherein said cells comprise pKB686 (ATCC deposite 39671) modified by the insertion of DNA comprising a structural gene.

20. The cell population of claim 12 wherein said cells comprise pKB730.

21. The cell population of claim 12 wherein said cells comprise pKB686 (ATCC deposit 39671) modified by converting the ClaI site to an XkoI site and inserting DNA comprising a structurals gene.

22. The cell population of claim 1 wherein said desired protein is T4 ligase.

23. The cell population of claim 1 wherein said cell chromosome comprises a defective lambda prophage with elements (a) and (b) of claim 1.

24. The cell population of claim 1 wherein said cells are KB204 (ATCC 39670) transformed with a plasmid comprising elements (c) and (d) of claim 1.

25. A method of fermentation of a desired product compound comprising:
(a) culturing the cells of claim 1 under said first environmental condition to a desired population of cells,
(b) changing said environmental condition to said second environmental condition,
(c) producing said compound under said second environemental condition.

26. The method of claim 25 wherein said desired product compound is said protein encoded by said protein-producing gene.

27. A gene comprising DNA capable of expressing a desired protein, said gene having an exogenous DNA attachment site of a lambda phage, said site being capable of synchronized site-specific recombination in the presence of a lambda phage enzyme system.

* * * * *